(12) United States Patent
Putzer et al.

(10) Patent No.: US 8,096,981 B2
(45) Date of Patent: Jan. 17, 2012

(54) HIP PANEL FOR A DISPOSABLE ABSORBENT ARTICLE AND METHOD OF MANUFACTURING SAME

(75) Inventors: Melissa Christine Putzer, Oshkosh, WI (US); Gary Lee Travis, Oshkosh, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 489 days.

(21) Appl. No.: 12/201,509

(22) Filed: Aug. 29, 2008

(65) Prior Publication Data

US 2010/0057035 A1 Mar. 4, 2010

(51) Int. Cl.
*A61F 13/15* (2006.01)

(52) U.S. Cl. ........ 604/394; 604/396; 604/387; 604/386; 604/385.3; 604/391; 604/390

(58) Field of Classification Search .................. 604/390, 604/391, 385.3, 386, 387, 394, 396, 385.24
See application file for complete search history.

(56) References Cited

U.S. PATENT DOCUMENTS

| | | |
|---|---|---|
| 3,901,236 A | 8/1975 | Assarsson et al. |
| 4,076,663 A | 2/1978 | Masuda et al. |
| 4,286,082 A | 8/1981 | Tsubakimoto et al. |
| 4,663,220 A | 5/1987 | Wisneski et al. |
| 4,704,116 A | 11/1987 | Enloe |
| 5,226,992 A | 7/1993 | Morman |
| 5,486,166 A | 1/1996 | Bishop et al. |
| 5,490,846 A | 2/1996 | Ellis et al. |
| 5,873,870 A | 2/1999 | Seitz et al. |
| 6,325,787 B1 | 12/2001 | Roe et al. |
| 2002/0107498 A1 | 8/2002 | Kling et al. |
| 2008/0103473 A1* | 5/2008 | Roe et al. ............. 604/385.24 |

FOREIGN PATENT DOCUMENTS

| | | |
|---|---|---|
| EP | 0217032 | 4/1987 |
| EP | 0888101 B1 | 5/2001 |
| EP | 1452158 A1 | 9/2004 |
| WO | 9428842 | 12/1994 |
| WO | 2007070333 | 6/2007 |

OTHER PUBLICATIONS

International Search Report & Written Opinion for PCT/IB2009/053692, dated Aug. 24, 2010, 10 pages.

* cited by examiner

*Primary Examiner* — Jacqueline F. Stephens
(74) *Attorney, Agent, or Firm* — Armstrong Teasdale LLC

(57) ABSTRACT

A disposable absorbent article includes an absorbent assembly having a bodyside liner, an outer cover, an absorbent structure, a first waist region, a second waist region, a crotch region, longitudinally opposite ends, and laterally opposite side edges. A pair of hip panels releaseably secures the first and second waist regions together. One of the hip panels extends laterally outward from one of the side edges in one of the first and second waist regions and the other hip panel extends laterally outward from the opposite side edge in the one of the first and second waist regions. Each of the hip panels has an upper edge, a lower edge, a fixed and a free end. Each of the upper and lower edges has a length and is curved along at least a portion of its length. The curved portions of the upper and lower edges are substantially identical.

21 Claims, 10 Drawing Sheets

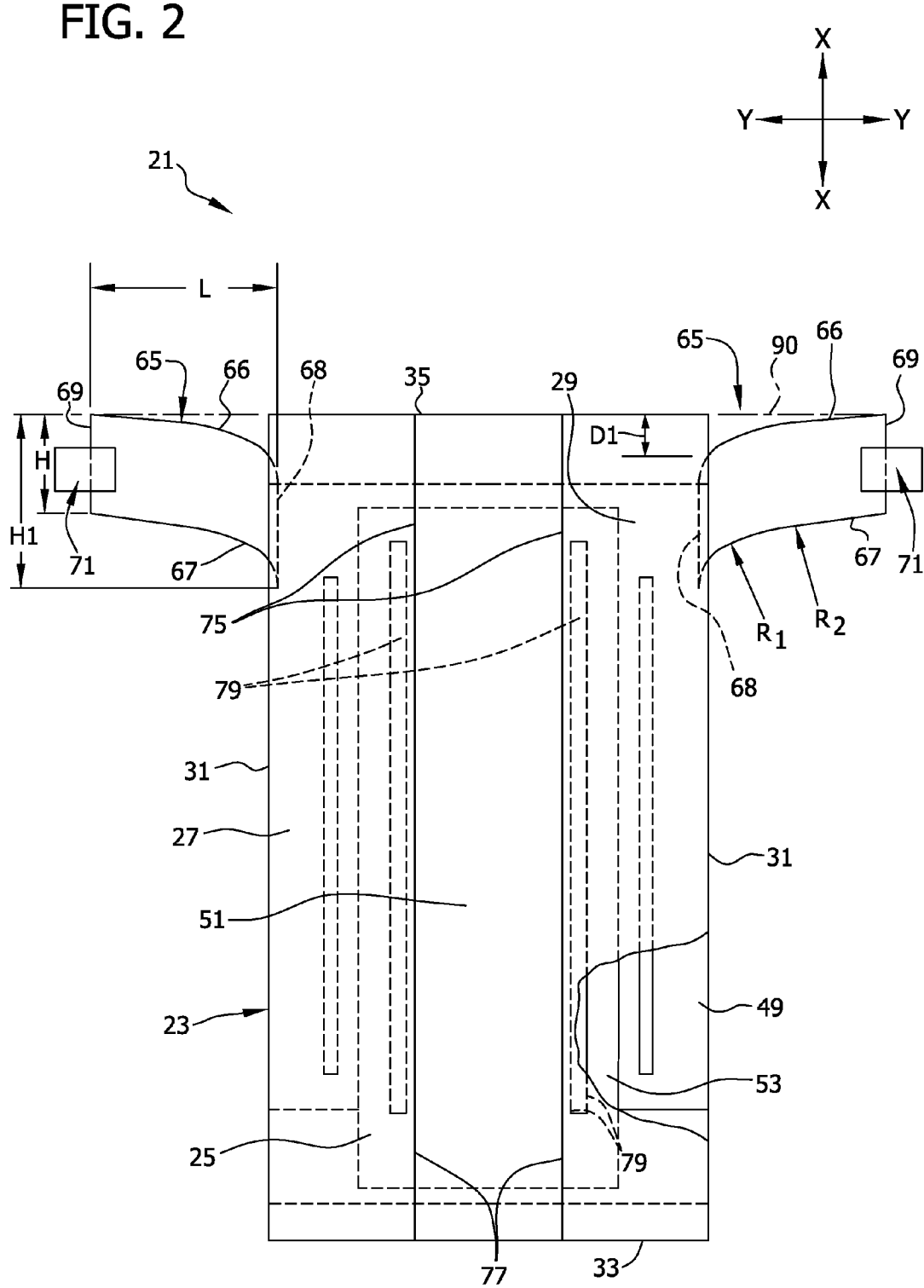

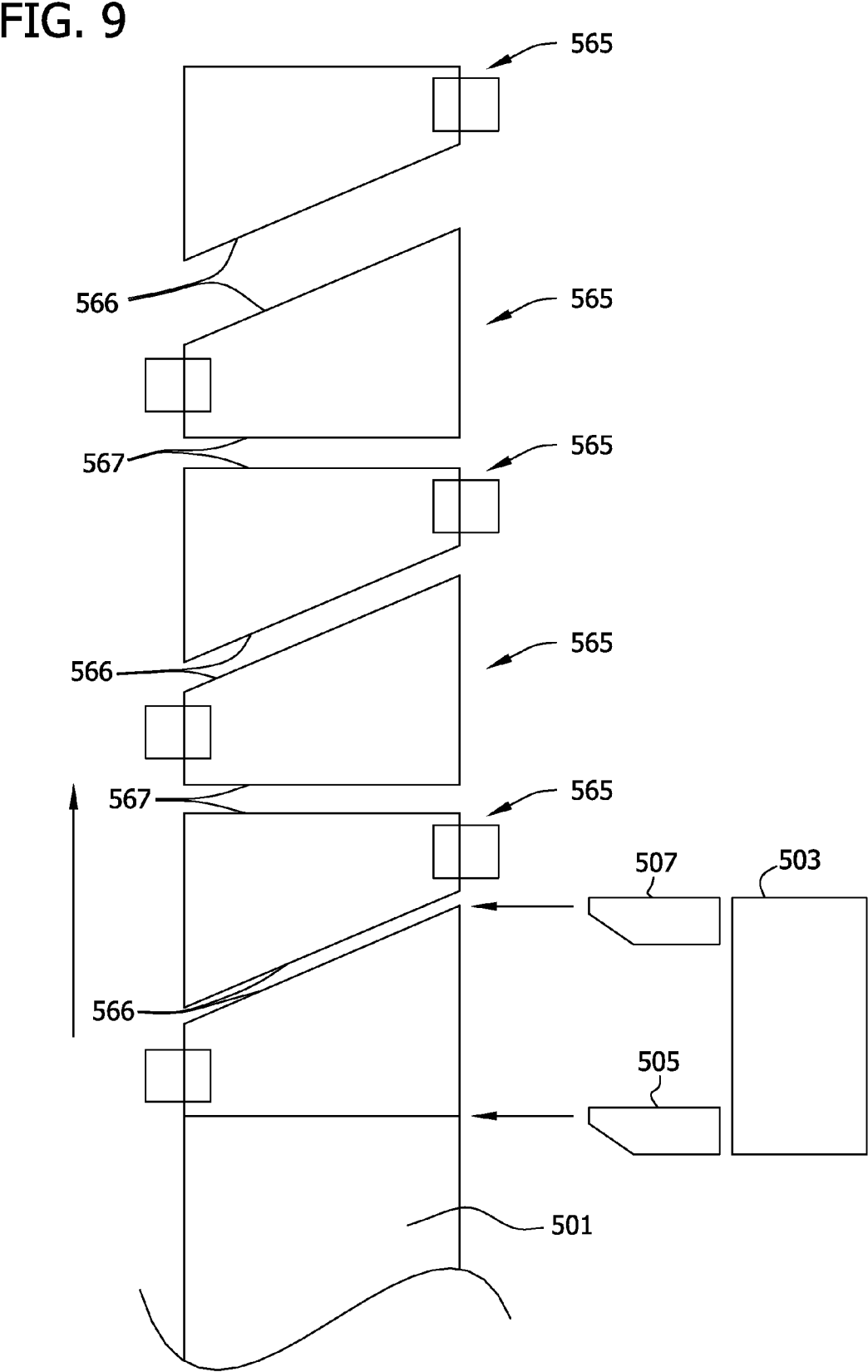

HIP PANEL FOR A DISPOSABLE ABSORBENT ARTICLE AND METHOD OF MANUFACTURING SAME

BACKGROUND

The field of this invention relates generally to disposable absorbent articles and more particularly to hip panels for disposable absorbent articles and a method of manufacturing the same.

Disposable absorbent articles, such as infant diapers, child training pants, adult incontinence briefs, and feminine hygiene products are well known for their use in absorbing and retaining liquid and/or solid discharges from the human body. Typically, absorbent articles include a permeable inner or bodyside liner, an impermeable outer cover, and an absorbent structure disposed intermediate the liner and the outer cover. The absorbent articles often have a front waist region, a back waist region, and a crotch region that extends longitudinally between and interconnects the front and back waist regions.

In some known absorbent articles, hip panels are secured to transversely opposite sides of the absorbent article in its back waist region for extending circumferentially about the wearer's hip region and securing the back waist region to the front waist region. That is, the hip panels circumferentially (e.g., transversely) interconnect the front and back waist regions of the absorbent article to define the leg openings of the article and support the article on the wearer's hips. In particular, when the absorbent article is worn, the hip panels overlie the respective hips of the wearer. As a result, a lower edge of the hip panels defines part of a leg opening of the absorbent article and is often curved or arcuate to match the contour of the wearer's upper thigh. An upper edge of the hip panel defines part of a waist opening of the absorbent article for encircling the waist of the wearer when the article is worn.

In one known method of manufacturing conventional hip panels, a web W of suitable hip panel material is continuously fed to a suitable cutting apparatus CA as illustrated schematically in FIG. 1A. The cutting apparatus CA performs a first cut to remove a generally semi-elliptical portion EP from one side of the web W to form a corresponding generally semi-elliptical cutout EC therein. The web W is subsequently severed (e.g., a second cut) at or near an apex A of the semi-elliptical cutout EP to form respective hip panels HP from the web for subsequent assembly with the rest of the absorbent article.

As a result of this manufacturing process, the hip panel HP has a curved upper edge UE and a curved lower edge LE. As seen in FIGS. 1A and 1B, for example, the upper edge UE of the hip panel HP curves in the opposite direction than the lower edge LE. More specifically, the upper edge UE of the conventional hip panel HP is curved downward while the lower edge LE is curved upward as viewed in FIG. 1A. A pair of the hip panels HP is then attached to the back waist region of the absorbent article (e.g., diaper D of FIG. 1B) for connecting the back waist region to the front waist region. Often, the back waist region is releasably connected to the front waist region using fastener components (FC), such as hook and loop fasteners.

It has been found that the downward curvature of the upper edge UE of the hip panel HP, which causes the fastener on the hip panel to be well below the end of the back waist region, may result in the caregiver inadvertently placing the front waist region of the absorbent article too low on the front of the wearer. It is believed that this misalignment is a result of caregivers having a general tendency or preference to align the hip panels and corresponding fasteners with the belly button region of the wearer. When this occurs, however, leakage, sagging, and drooping of the absorbent article is more likely to occur. In addition, misalignment compromises the overall comfort of the absorbent article and may cause redmarking of the wearer's skin along the hip region.

Moreover, the conventional manufacturing process for forming hip panels results in significant portions of the web being wasted. In the illustrated embodiment of FIG. 1, for example, each of the semi-elliptical portions EP cut from the web W result in unusable waste. Furthermore, conventional hip panels often have a significant maximum height, particularly at the end of the hip panel that is permanently attached to the back waist region of the article. In the illustrated embodiment of FIGS. 1A and 1B, for example, the hip panels have a maximum height of about 91 mm, thus requiring a substantial amount of material to make the hip panel.

There is a need, therefore, for a hip panel for an absorbent article that facilitates proper alignment of the absorbent article during its placement on the wearer and is manufactured using less material and without producing waste.

SUMMARY

In one aspect, a disposable absorbent article generally comprises an absorbent assembly having a bodyside liner, an outer cover, an absorbent structure disposed intermediate the liner and the outer cover, a first waist region, a second waist region, a crotch region disposed longitudinally between and interconnecting the first waist region and the second waist region, longitudinally opposite ends, and laterally opposite side edges. A pair of hip panels releaseably secures the first and second waist regions of the absorbent assembly together in a wear configuration of the article. One of the hip panels extends laterally outward from one of the side edges in one of the first and second waist regions of the absorbent assembly and the other hip panel extends laterally outward from the opposite side edge in the one of the first and second waist regions of the absorbent assembly. Each of the hip panels comprises an upper edge, a lower edge, a fixed end attached to one of the first and second waist regions, and a free end. Each of the upper and lower edges has a length and is curved along at least a portion of its length. The curved portions of the upper and lower edges are identical with respect to each other. A fastener component is secured to each of the hip panels.

In another aspect, a disposable absorbent article generally comprises an absorbent assembly having a bodyside liner, an outer cover, an absorbent structure disposed intermediate the liner and the outer cover, a first waist region, a second waist region, a crotch region disposed longitudinally between and interconnecting the first waist region and the second waist region, longitudinal opposite ends, and laterally opposite side edges. A pair of hip panels releaseably secures the first and second waist regions of the absorbent assembly together in a wear configuration of the article. One of the hip panels extends laterally outward from one of the side edges in one of the first and second waist regions of the absorbent assembly and the other hip panel extends laterally outward from the opposite side edge in the one of first and second waist regions of the absorbent assembly. Each of the hip panels has a fixed end attached to the absorbent assembly at a location inward from the longitudinal end in the one of first and second waist regions, and a free end disposed closer to a line including the longitudinal end in the one of first and second waist regions than the fixed end in a laid-flat configuration of the article.

In yet another aspect, a method for manufacturing a hip panel for a disposable absorbent article generally comprises feeding a web to a cutting apparatus. The web is cut at a first location with the cutting apparatus to form a curved lower edge of the hip panel. The web is cut at a second location with the cutting apparatus to form a curved upper edge of the hip panel. The curved lower edge and the curved upper edge are substantially identical with respect to each other.

BRIEF DESCRIPTION OF THE DRAWINGS

FIG. 2 is a plan view of a diaper in its unfastened and laid flat configuration to show an inner surface of the diaper which faces the wearer when the diaper is worn.

FIG. 9 is a schematic of a method of manufacturing yet another embodiment of hip panels from a web.

DETAILED DESCRIPTION OF THE DRAWINGS

Figure 1A:
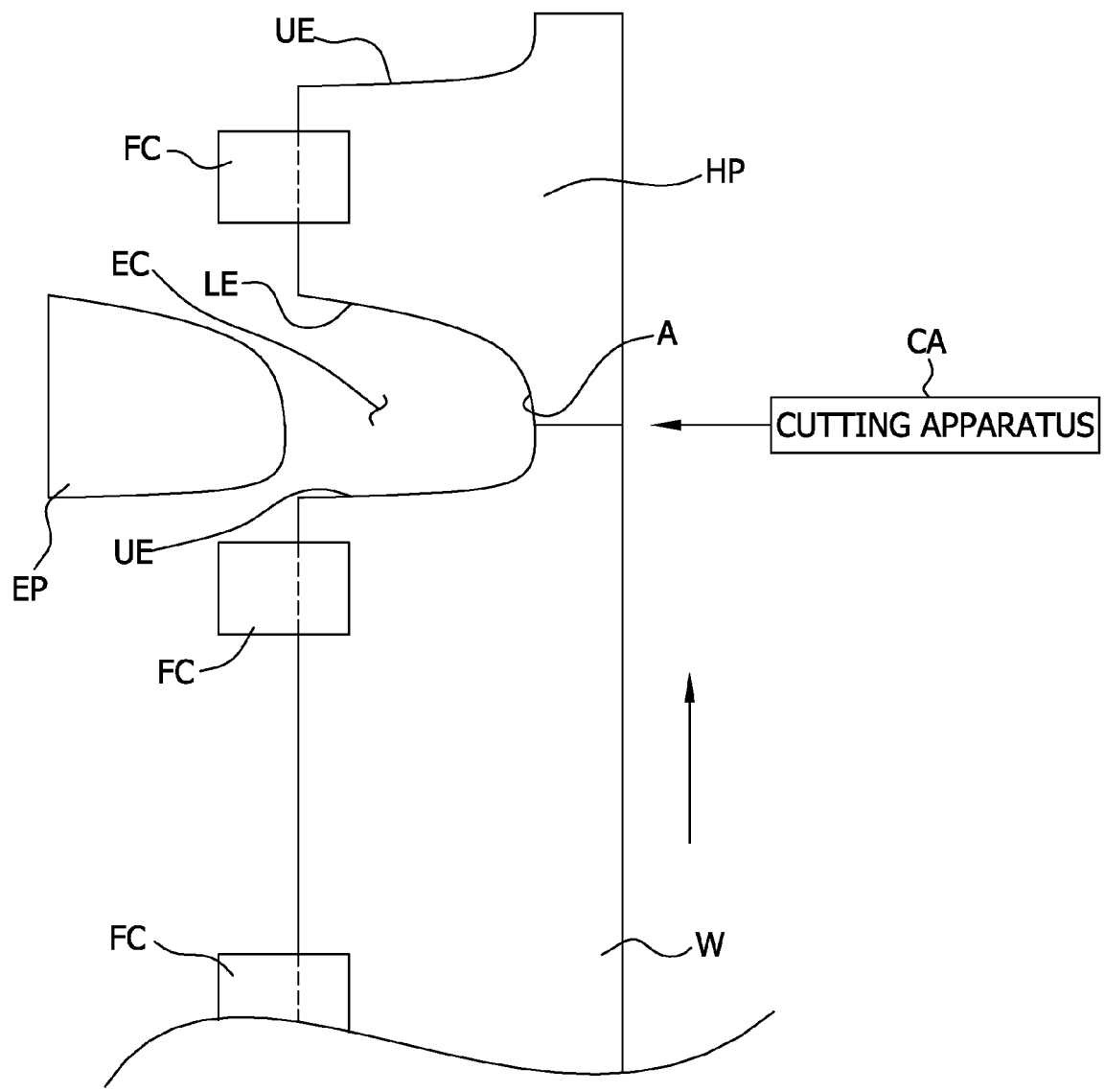
FIG. 1A is a schematic of a prior art method of manufacturing hip panels from a web.
Figure 1B:
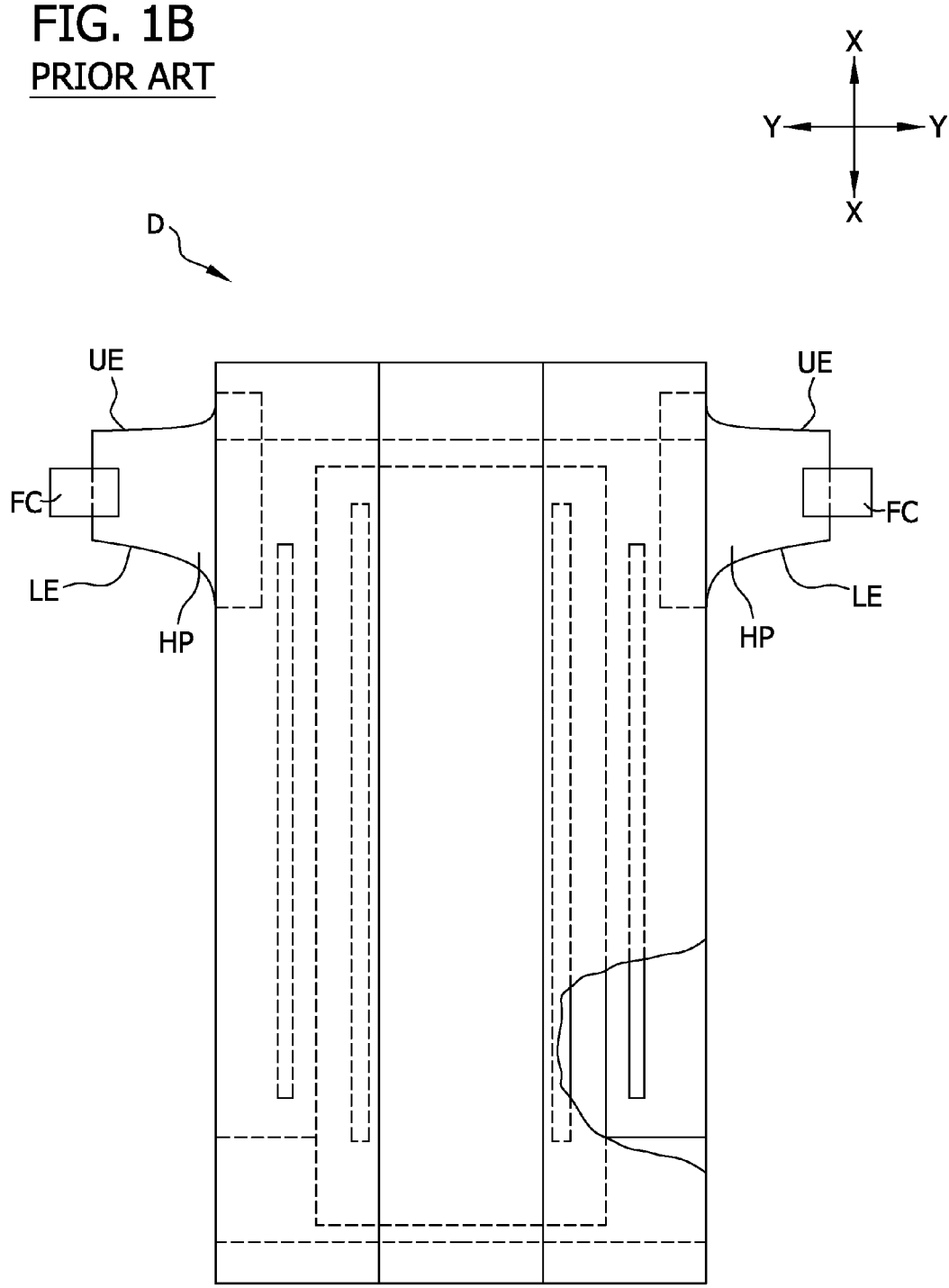
FIG. 1B is a plan view of a diaper in its unfastened and laid flat configuration to show an inner surface of the diaper which faces the wearer when the diaper is worn, the diaper having the prior art hip panels of FIG. 1A.
Figure 3:
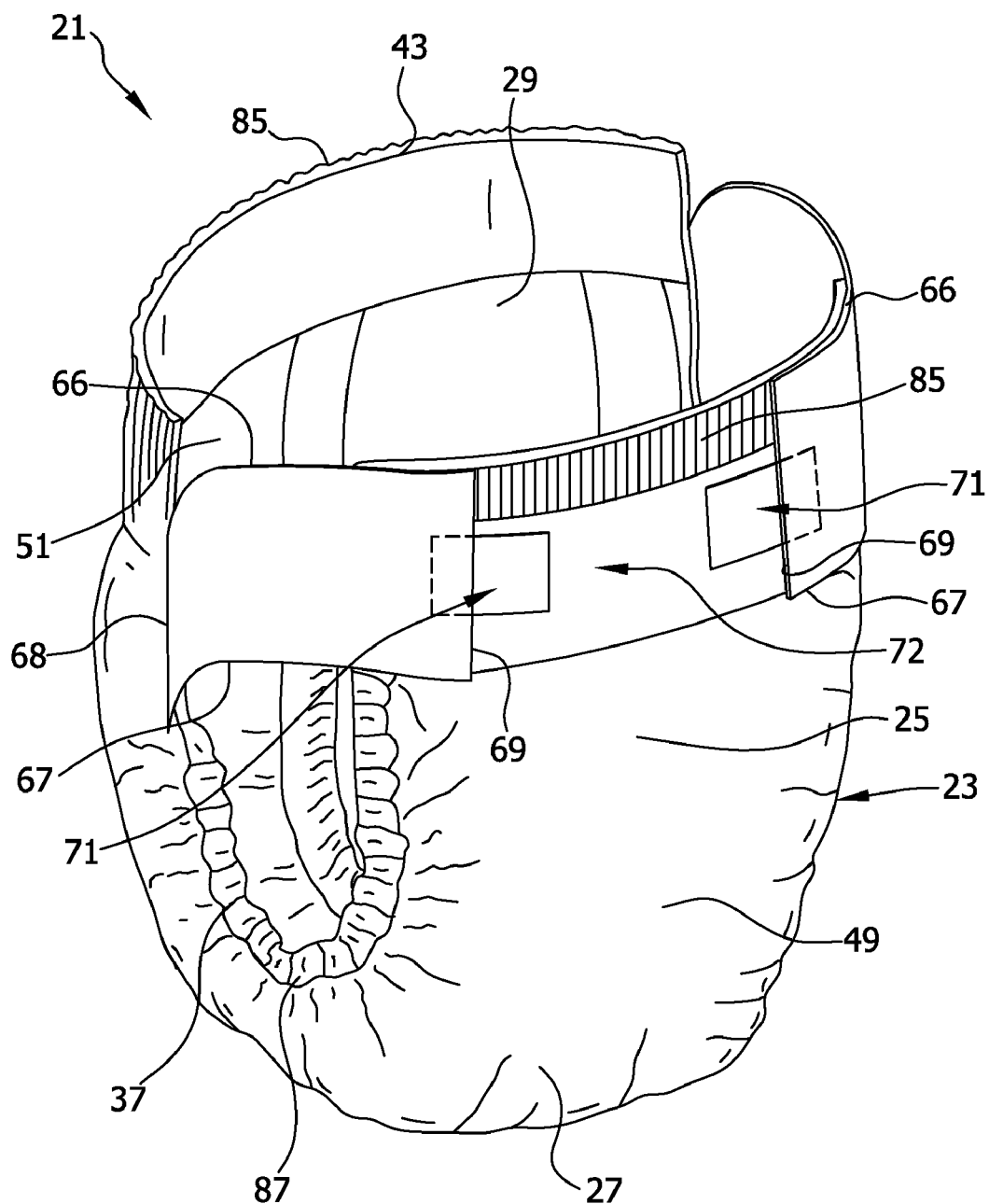
FIG. 3 is a perspective view of the diaper in its fastened, wear configuration.

Referring now to the drawings, FIGS. 2 and 3 illustrate one embodiment of a disposable absorbent article in the form of a diaper, indicated generally at 21. The diaper 21 in FIG. 1 is in an unfolded and laid-flat configuration to illustrate a longitudinal axis X and a lateral axis Y of the diaper. The diaper 21 generally comprises an absorbent assembly, indicated generally at 23, having a front (e.g., anterior) waist region 25, a crotch (e.g., central) region 27, and a back (e.g., posterior) waist region 29. The front waist region 25 generally includes the portions of the absorbent assembly 23 which extend over the wearer's lower abdominal region and the back waist region 29 generally includes the portions of the absorbent assembly which extend over the wearer's lower back waist region. The crotch region 27 includes the portion extending longitudinally through the wearer's crotch from the front waist region 25 to the back waist region 29 and laterally between the wearer's legs. It is contemplated that the absorbent article can be in the form of an adult incontinence article or a training pant instead of the diaper described herein without departing from the scope of the invention.

The absorbent assembly 23 is generally rectangular and has laterally opposite side edges 31 and longitudinally opposite front and rear waist edges or ends, respectively designated 33 and 35. It is understood, however, that the diaper 21 may have other shapes, such as an I-shape or a T-shape without departing from the scope of the present invention. The side edges 31 of the diaper 21 extend longitudinally from the front waist region 25 through the crotch region 27 to the back waist region 29 for forming transversely spaced leg openings 37 (one of the leg openings being seen in FIG. 3) of the diaper when worn. As worn on the wearer's body, the diaper 21 further defines a central waist opening 43 for receiving the waist of the wearer.

As seen in FIG. 2, the absorbent assembly 23 of the diaper 21 comprises an outer cover 49, a bodyside liner 51 positioned in opposed relationship with the outer cover, and an absorbent structure 53 disposed between the outer cover and the liner. In one embodiment, the outer cover 49 is stretchable and may or may not be somewhat elastic. More suitably, the outer cover 49 is sufficiently extensible such that once stretched under the weight of the insulted absorbent structure, the outer cover will not retract substantially back toward its original position. However, it is contemplated that the outer cover 49 may instead be generally non-extensible and remain within the scope of this invention.

The outer cover 49 may be a multi-layered laminate structure to provide desired levels of extensibility as well as liquid impermeability and vapor permeability. For example, the outer cover 49 of the illustrated embodiment is of two-layer construction, including an outer layer constructed of a vapor permeable material and an inner layer constructed of a liquid impermeable material, with the two layers being secured together by a suitable laminate adhesive. It is understood, however, that the outer cover 49 may instead be constructed of a single layer of liquid impermeable material, such as a thin plastic film, without departing from the scope of this invention. The liquid impermeable inner layer of the outer cover 49 can be either vapor permeable (i.e., "breathable") or vapor impermeable.

The bodyside liner 51 is suitably pliable, soft feeling, and nonirritating to the wearer's skin, and is employed to help isolate the wearer's skin from the absorbent structure 53. The liner 51 is less hydrophilic than the absorbent structure 53 to present a relatively dry surface to the wearer, and is sufficiently porous to be liquid permeable to thereby permit liquid to readily penetrate through its thickness. A suitable bodyside liner 51 may be manufactured from a wide selection of web materials, but is suitably capable of stretching in at least one direction (e.g., longitudinal or lateral). In particular embodiments, the bodyside liner 51 is extensible and capable of extending along with the outer cover 49 for desired fit of the diaper 21 on the wearer.

The diaper 21 illustrated in FIG. 2 also comprises a pair of containment flaps 75 configured to provide a barrier to the lateral flow of body exudates. The containment flaps 75 are located generally adjacent laterally opposite side edges 31 of the diaper 21 and, when the diaper is laid flat as shown in FIG. 2 extend inward toward the longitudinal axis X of the diaper. Each containment flap 75 typically has a free, or unattached end 77 free from connection with the bodyside liner 51 and other components of the diaper 21. Elastic strands 79 disposed within the flaps 75 adjacent the unattached ends thereof urge the flaps toward an upright, perpendicular configuration in at least the crotch region 27 of the diaper 21 to form a seal against the wearer's body when the diaper is worn. The containment flaps 75 may extend longitudinally the entire length of the diaper 21 or they may extend only partially along the length of the diaper. When the containment flaps 75 are shorter in length than the diaper 21, the flaps can be selectively positioned anywhere between the side edges 31 of the diaper 21 in the crotch region 27. In a particular aspect of the invention, the containment flaps 75 extend the entire length of the diaper 21 to better contain the body exudates.

Such containment flaps 75 are generally well known to those skilled in the art and therefore will not be further described herein. As an example, suitable constructions and arrangements for containment flaps 75 are described in U.S.

Pat. No. 4,704,116 issued Nov. 3, 1987, to K. Enloe, the disclosure of which is hereby incorporated by reference. The diaper 21 may also incorporate other containment components in addition to or instead of the containment flaps 75. For example, while not shown in the drawings, other suitable containment components may include, but are not limited to, elasticized waist flaps, foam dams in the front, back and/or crotch regions, and the like.

The absorbent structure 53 is generally compressible, conformable, non-irritating to the wearer's skin, and capable of absorbing and retaining body exudates. The absorbent structure 53 may be constructed of any of a number of absorbent materials, as are well known in the art. For example, the absorbent structure 53 may include coform, meltblown fibers, bonded carded webs, a wetlaid body, tissue laminates, foams, a surge/air formed composite and the like or combinations thereof.

Examples of suitable fibers for use in the absorbent structure 53 include naturally occurring organic fibers composed of intrinsically wettable material, such as cellulosic fibers including wood pulp fibers which can be curled, crosslinked or otherwise mechanically or chemically modified. Other examples of suitable fibers include synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a non-wettable thermoplastic polymer, such as polypropylene fibers, which have been hydrophilized by appropriate means. The fibers may be hydrophilized, for example, by treatment with silica, treatment with a material that has a suitable hydrophilic moiety and is not readily removable from the fiber, or by sheathing the nonwettable, hydrophobic fiber with a hydrophilic polymer during or after the formation of the fiber. It is contemplated that selected blends of the various types of fibers mentioned above may also be employed.

High-absorbency material can also be used in the absorbent structure 53 and may include absorbent gelling materials, such as superabsorbent materials. Absorbent gelling materials can be natural, biodegradable, synthetic and modified natural polymers and materials. In addition, the absorbent gelling materials can be inorganic materials, such as silica gels, or organic compounds such as cross-linked polymers. Such means can include, for example, physical entanglement, crystalline domains, covalent bonds, ionic complexes and associations, hydrophilic associations, such as hydrogen bonding, and hydrophobic associations or Van der Waals forces. Examples of synthetic absorbent gelling material polymers include the alkali metal and ammonium salts of poly(acrylic acid) and poly(methacrylic acid), poly (acrylamides), poly(vinyl ethers), maleic anhydride copolymers with vinyl ethers and alpha-olefins, poly(vinyl pyrrolidone), poly(vinylmorpholinone), poly(vinyl alcohol), and mixtures and copolymers thereof.

Further polymers suitable for use in the absorbent core include natural and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum and the like. Mixtures of natural and wholly or partially synthetic absorbent polymers can also be useful in the present invention. Other suitable absorbent gelling materials are disclosed by Assarsson et al. in U.S. Pat. No. 3,901,236 issued Aug. 26, 1975. Processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al.

The diaper 21 can also include a surge management layer (not shown) which helps to decelerate and diffuse surges or gushes of liquid that may be rapidly introduced into the absorbent structure 53. Desirably, the surge management layer can rapidly accept and temporarily hold the liquid prior to releasing the liquid to the absorbent structure. In the illustrated embodiment, for example, a surge layer can be located between the absorbent structure 53 and the bodyside liner 51. Examples of suitable surge management layers are described in U.S. Pat. No. 5,486,166 entitled FIBROUS NON-WOVEN WEB SURGE LAYER FOR PERSONAL CARE ABSORBENT ARTICLES AND THE LIKE by C. Ellis and D. Bishop, which issued Jan. 23, 1996, and U.S. Pat. No. 5,490,846 entitled IMPROVED SURGE MANAGEMENT FIBROUS NON-WOVEN WEB FOR PERSONAL CARE ABSORBENT ARTICLES AND THE LIKE by C. Ellis and R. Everett, which issued Feb. 13, 1996, the entire disclosures of which are hereby incorporated by reference in a manner that is consistent herewith.

To provide improved fit and to help further reduce leakage of body exudates from the diaper 21, elastic components are typically incorporated therein, particularly at the waist area and the leg areas. For example, the diaper 21 of the illustrated embodiment has waist elastic components 85 and leg elastic components 87 (FIG. 3). The waist elastic components 85 are configured to gather and shirr the end margins of the diaper 21 to provide a resilient, comfortable close fit around the waist of the wearer and the leg elastic components 87 are configured to gather and shirr the side margins of the diaper at the leg openings 37 to provide a close fit around the wearer's legs.

A pair of hip panels, each panel being indicated generally at 65, is secured to the absorbent assembly 23 generally at the back waist region 29 thereof with the hip panels extending laterally outward from adjacent the respective opposite side edges 31 of the assembly. As illustrated in FIG. 2, for example, one of the hip panels 65 extends laterally outward from adjacent one of the side edges 31 in the back waist region 29 of the absorbent assembly 23 and the other hip panel extends laterally outward from adjacent the opposite side edge in the back waist region of the absorbent assembly.

The hip panels 65 may be attached to the outer cover 49 as illustrated, to the bodyside liner 51, between the outer cover and liner, or to other components of the diaper 21. The hip panels 65 may also be stretchable, elastic, or otherwise elastomeric. For example, the hip panels 65 may be an elastomeric material such as a neck-bonded laminate (NBL) or stretch-bonded laminate (SBL) material. Methods of making such materials are well known to those skilled in the art and are described, for example, in U.S. Pat. No. 4,663,220 issued May 5, 1987 to Wisneski et al., U.S. Pat. No. 5,226,992 issued Jul. 13, 1993 to Morman, and European Patent Application No. EP 0 217 032 published on Apr. 8, 1987 in the names of Taylor et al., the disclosures of which are hereby incorporated by reference. In one potential embodiment, the hip panels 65 may be formed integrally with a selected diaper component. For example, the hip panels 65 may be formed integrally with the outer cover 49 or the bodyside liner 51. In another suitable embodiment, the hip panels 65 are formed separate from the other components of the diaper 21 and secured thereto, such as by bonding, adhesive or other suitable attachment technique.

Fastening components, such as hook and loop fasteners, designated 71 and 72 respectively, are used to secure the diaper 21 in its wear configuration. Alternatively, other fastening components (not shown), such as buttons, pins, snaps, adhesive tape fasteners, cohesives, mushroom-and-loop fasteners, or the like, may be employed. Desirably, the interconnection of the fastening components 71, 72 is selectively releasable and re-attachable. In the illustrated embodiment of FIGS. 2 and 3, the hook fasteners 71 are secured to and extend laterally outward from the respective hip panels 65 at the back waist region 29 of the diaper 21. In the illustrated embodiment, the hook fasteners 71 are generally rectangular but it is understood that the fasteners can have different shapes. It is understood that the hook components 71 can be secured to the respective hip panel 65 within the boundary of the hip panel such as adjacent to the laterally outermost edge of a free end 69. It is also understood that the hip panels 65 may be formed of a hook material and thus comprise the hook fasteners 71 without departing from the scope of this invention. That is, the hook fasteners 71 can be integral with the hip panels 65.

The loop fastener 72 of the illustrated diaper 21 is a panel of loop material secured to the outer cover 49 at the front waist region 25 of the diaper 21 to provide a "fasten anywhere" mechanical fastening system for improved fastening of the hook fasteners 71 with the loop fastener. It is contemplated that, in other embodiments, the loop fastener 72 may be formed integral with the outer cover 49. In other words, the outer cover 49 (such as the outer layer thereof) can be made in part or in whole from a loop material. It is also contemplated that the loop fasteners 72 can be formed integral with or attached to the hip panels 65 and the hook fasteners 71 formed integral with or attached to the outer cover 49.

As illustrated in FIGS. 2 and 3, each of the hip panels comprises (relative to the orientation of the diaper as illustrated) an upper edge 66, a lower edge 67, and two side edges defining a fixed end 68 and the free end 69 of the hip panel. Each of the hip panels 65 is secured (e.g., bonded) at its fixed end 68 to one of the respective laterally opposite sides of the absorbent assembly 23 in its back waist region 29. The free ends 69 of the hip panels 65 have the hook fastener component 71 attached adjacent thereto. In one suitable embodiment, such as for a diaper, the free ends 69 of each of the hip panels 65 have a height H in the range between about 25 mm and about 100 mm. In one particularly suitable embodiment, the height H of the free ends 69 of each of the hip panels 65 is about 65 mm. In the illustrated embodiment, the hip panels have a uniform height along their length (e.g., from their fixed end 68 to their free end 69). As a result, the fixed ends 68 of the hip panels have the same height as the free ends 69. It is contemplated, however, that the hip panels can vary in height along their lengths and that the fixed ends 68 can have heights that differ from the free ends 69 without departing from the scope of this invention. It is also understood that these dimensions will vary depending on the intended purpose of the article, such as for an adult incontinence article.

Each of the hip panels 65 also includes an overall height H1 that is defined by its maximum projected height. In the illustrated embodiment, for example, the overall height H1 of each of the hip panels 65 is defined as the projected height from the intersection of the fixed end 68 and the lower edge 67 to the intersection of the free end 69 and the upper edge 66 (FIG. 2). In one suitable embodiment, such as for a diaper, the overall height H1 of each of the hip panels is in the range between about 25 mm and about 170 mm. In one particularly suitable embodiment, the overall height H1 of the hip panels 65 is about 100 mm to provide a comfortable fit on wearer's hips while inhibiting sagging and droop of the article. In another particularly suitable embodiment, the overall height H1 of the hip panels 65 is about 55 mm to reduce waste and cost while still inhibiting sagging and droop. In one suitable embodiment, the ratio of the overall height H1 of the hips panels 65 to their height at their respective free ends 69 is greater than 1. In a particularly suitable embodiment, the ratio of the overall height H1 to the height at the respective free end 69 is in the range of about 1.5 and 2.25. In a more particularly suitable embodiment, the ratio of the overall height H1 of the hip panels 65 to their height at their respective free end 69 is approximately 1.75.

Each of the upper and lower edges 66, 67 of the hip panels 65 has a length L and is curved along at least a portion of its length. In the illustrated embodiment, the curved portions of the upper and lower edges 66, 67 are identical with respect to each other. More specifically, the curved portions of the illustrated upper and lower edges 66, 67 comprise a first radius of curvature R1 adjacent the fixed end 68 and a second radius of curvature R2 adjacent the free end 69. The first radius of curvature R1 is greater than the second radius of curvature R2. As a result, the curvature of the hip panels 65 is greatest near the back waist region 29 of the absorbent assembly 23 and decreases as it extends outward toward its free side edge 68. In the illustrated embodiment, the upper and lower edges 66, 67 of hip panels 65 are almost straight near the free end 69—angling longitudinally and laterally outward relative to the absorbent assembly 23. It is contemplated, however, that the radius of curvatures can be greater or less than those illustrated in the accompanying figures. It is also understood that the upper and lower edges 66, 67 may be other than curved and remain with the scope of this invention.

The hip panels 65 each have an overall length L in the range from about 50 mm to about 120 mm. In one suitable embodiment, for example, each hip panel 65 has an overall length L of about 82 mm. The overall length L is defined as the length of the hip panel 65 as measured from its fixed end 68 to its free end 69. Each of the hip panels 65 also include a useable length defined as the distance between the free end 69 of the respective hip panel and the adjacent lateral side edge 31 of the absorbent assembly 23.

As seen in FIG. 2, each of the hip panels 65, and more specifically the upper edge 66 of the hip panel is offset longitudinally from the longitudinal end 35 of the absorbent assembly 23 in the back waist region 29 of the absorbent assembly a distance D1 in the range of about 0 mm to about 45 mm in a laid flat configuration of the diaper 21. In one suitable embodiment, the distance D1 between the longitudinal end 35 in the back waist region 29 of the absorbent assembly 23 and the upper edge 66, each of the hip panels 65 is about 35 mm. As described above and illustrated in FIG. 3, at least the upper edges 66 of the hip panels 65 curve upward as they extend away from the absorbent assembly 23. In the illustrated embodiment, the curvature of the hip panel upper edge 66 and the distance D1 between the longitudinal end 35 of the absorbent assembly 23 in its back waist region 29 and the upper edge 66 of the hip panels 65 at the attachment end of the hip panel is such that the free ends 69 of the hip panels do not extend longitudinally outward beyond a line 90 including the longitudinal end 35 of the absorbent assembly 23. It is understood, however, that the free ends 69 of the hip panels 65 can extend longitudinally outward beyond the line 90 including the longitudinal end 35 of the absorbent assembly 23.

As illustrated in FIG. 3, the hip panels 65 releaseably secure the front and back waist regions 25, 29 of the absorbent assembly 23 together to define a wear configuration of the diaper 21. It has been found that the curved hip panels 65 positively influence the placement of the diaper 21 of the wearer. More specifically, the upward curved hip panels 65 facilitate securement of the fastener components of the hip panels higher on the front waist region 25 (nearer the longitudinal end 33 of the absorbent assembly) of the absorbent article 23. For example, as illustrated in FIG. 3, the upper edges 66 of the hip panels 65 are generally aligned with the longitudinal end 33 of the absorbent assembly 23 in the wear configuration of the diaper 21. Thus, in some embodiments the diapers 21 would be less prone to sagging and/or drooping, which can result in leakage. Moreover, attaching the hip panels 65 higher on the front waist region 25 results in a better and more comfortable fit for the wearer. Furthermore, the hip panels 65 can be manufactured with a significantly reduced height, particularly at the fixed end 68 thereof, as compared to the prior art hip panels.

Figure 4:
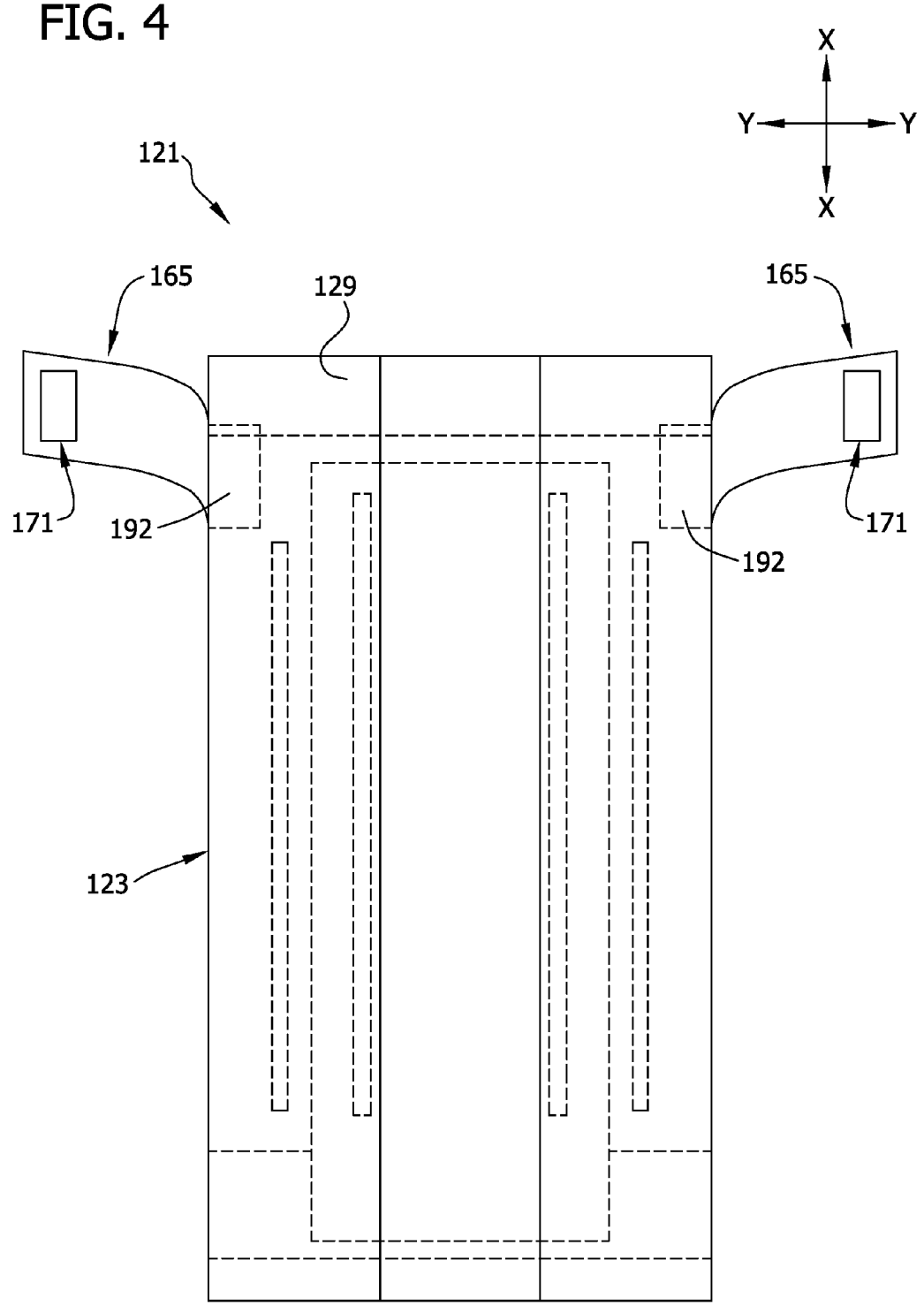
FIG. 4 is a plan view of another embodiment of a diaper in its unfastened and laid flat configuration to show an inner surface of the diaper which faces the wearer when the diaper is worn.
Figure 5:
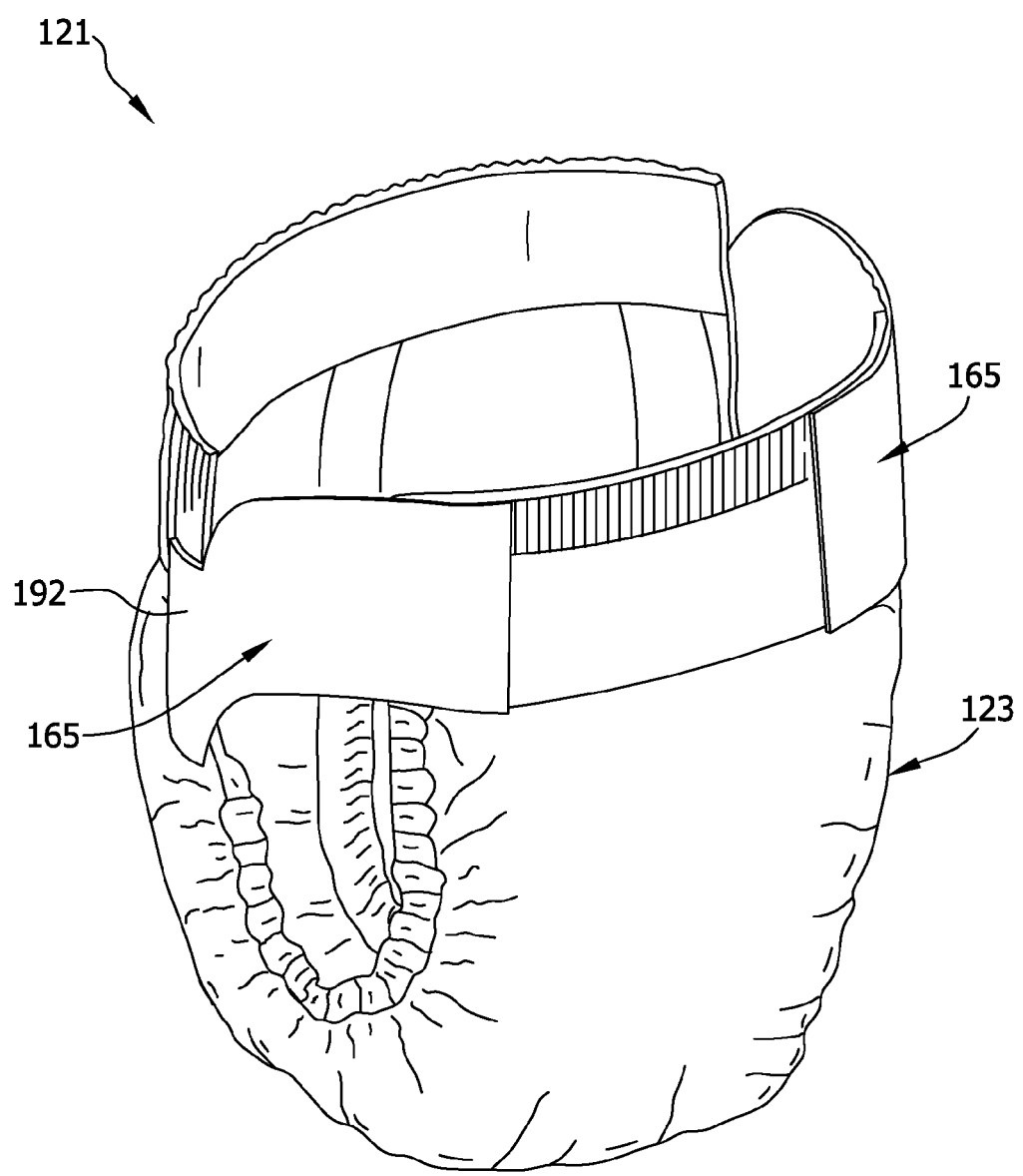
FIG. 5 is a perspective view of the diaper of FIG. 4 in its fastened, wear configuration.

FIGS. 4 and 5 illustrate a diaper 121 having another suitable embodiment of hip panels 165. The hip panels 165 of FIGS. 4 and 5 are similar to those illustrated in FIGS. 2 and 3 except that each of these hip panels includes an attachment portion 192 for bonding the hip panel 165 to the back waist region 129 of the absorbent assembly 123. In the illustrated embodiment, the attachment portions 192 are generally rectangular but it is understood that they can have different shapes. Fastener components 171 (e.g., hook fasteners) are secured to the each of the hip panels 165 within the boundaries of the respective hip panel.

Figure 6:
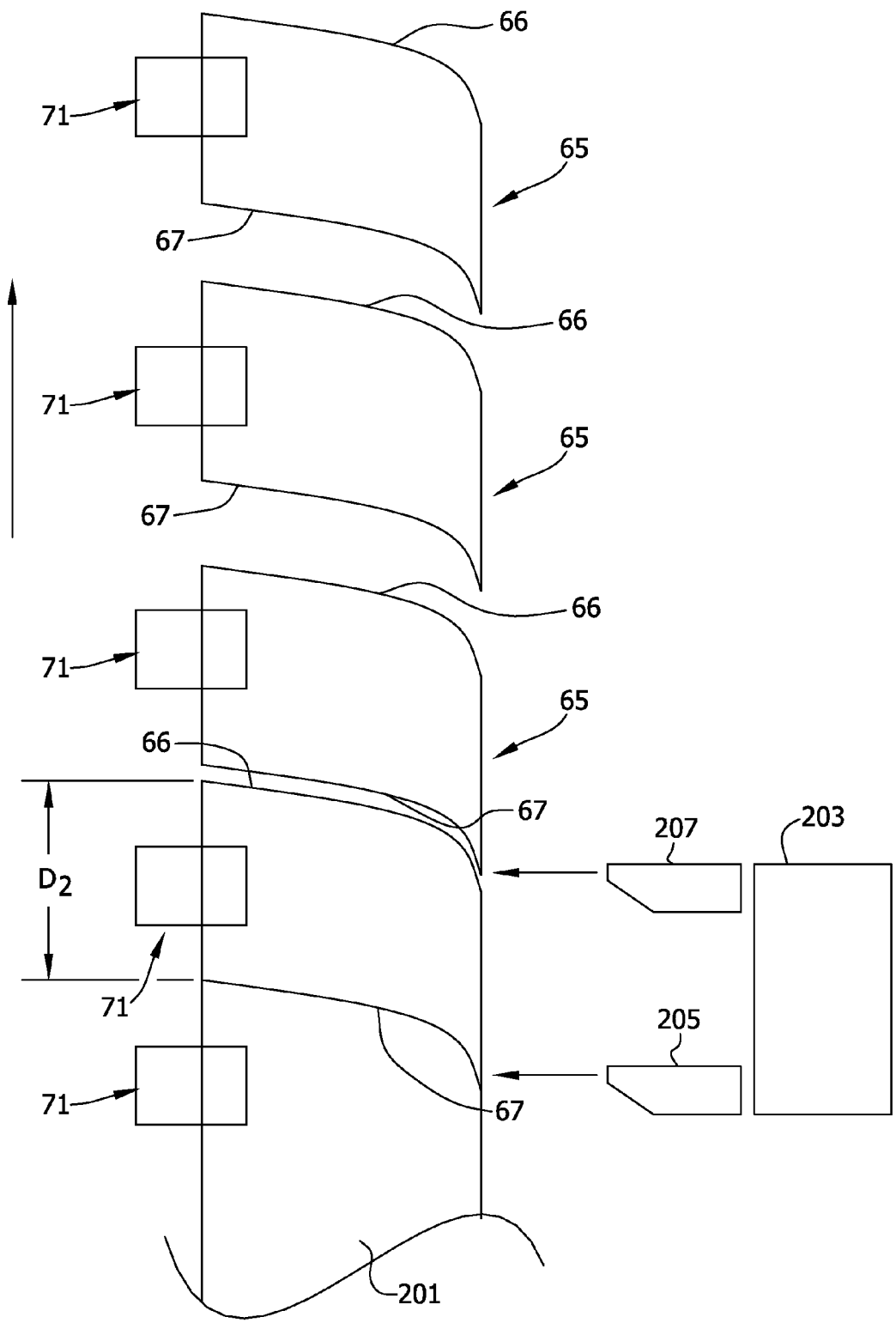
FIG. 6 is a schematic of a method of manufacturing the hip panels of FIGS. 1 and 2 from a web.

FIG. 6 schematically illustrates one embodiment for manufacturing the hip panels 65 illustrated in FIGS. 2 and 3. A continuous web 201 of material suitable for use as hip panel material is fed to a cutting apparatus 203 in a machine direction as illustrated by a direction arrow in FIG. 6. The web 201 is cut at a first location 207 with the cutting apparatus 203 to concurrently form the curved lower edge 67 of a leading hip panel 65 and the curved upper edge 66 of a trailing hip panel 65. The web 201 is subsequently cut at a second location 205 with the cutting apparatus 203 to form the curved lower edge 67 of the trailing hip panel 65 (as well as the upper edge 66 of the next trailing hip panel). A distance D2 between the first and second locations 207, 205 of the web 201 that are cut is in the range between about 25 mm and about 100 mm. In one suitable embodiment, the distance D2 between the first and second locations is about 65 mm.

It is understood that a single cutting apparatus 203 or two, separate cutting apparatus can be used to cut the web at the first and second locations 207, 205. It is also understood that the two cuts in the web can occur separately or simultaneously. As seen in FIG. 6, the entire web 201 is used in manufacturing the hip panels 65. That is, no wasted web material is produced.

As illustrated in FIG. 6, fastener components 71 have been bonded to the web 201 before the web is cut by the cutting apparatus 203. It is contemplated, however, that the fastener components 71 may be bonded to the hip panels 65 (e.g., after cutting) instead of to the web 201.

After the hip panels 65 are formed, they may be bonded (or otherwise permanently attached) to the absorbent assembly 23. More specifically, the hip panels 65 are bonded adjacent one of the absorbent assembly side edges 31 in the back waist region 29 of the absorbent assembly 23 and the other hip panel is bonded adjacent the opposite side edge in the back waist region of the absorbent assembly. In one suitable embodiment, each of the hip panels 65 is bonded to the absorbent assembly 23 with the upper edge of the hip panel offset longitudinally about 0 mm and about 45 mm from the longitudinal end 35 of the absorbent assembly in its back waist region 29. In a particularly suitable embodiment, this offset is about 35 mm from the longitudinal end 35 of the absorbent assembly 23 in its back waist region 29.

Figure 7:
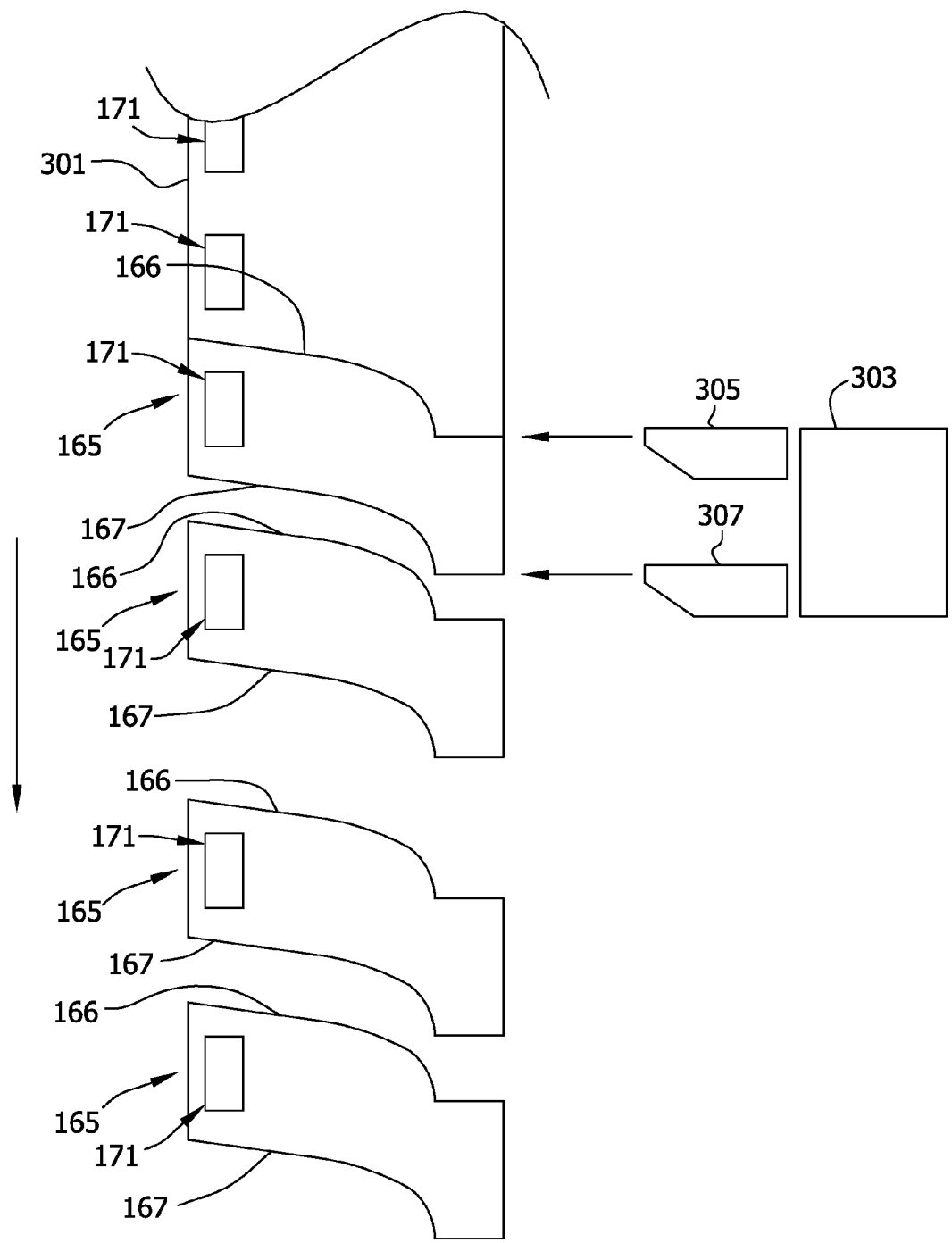
FIG. 7 is a schematic of a method of manufacturing the hip panels of FIGS. 3 and 4 from a web.
Figure 8:
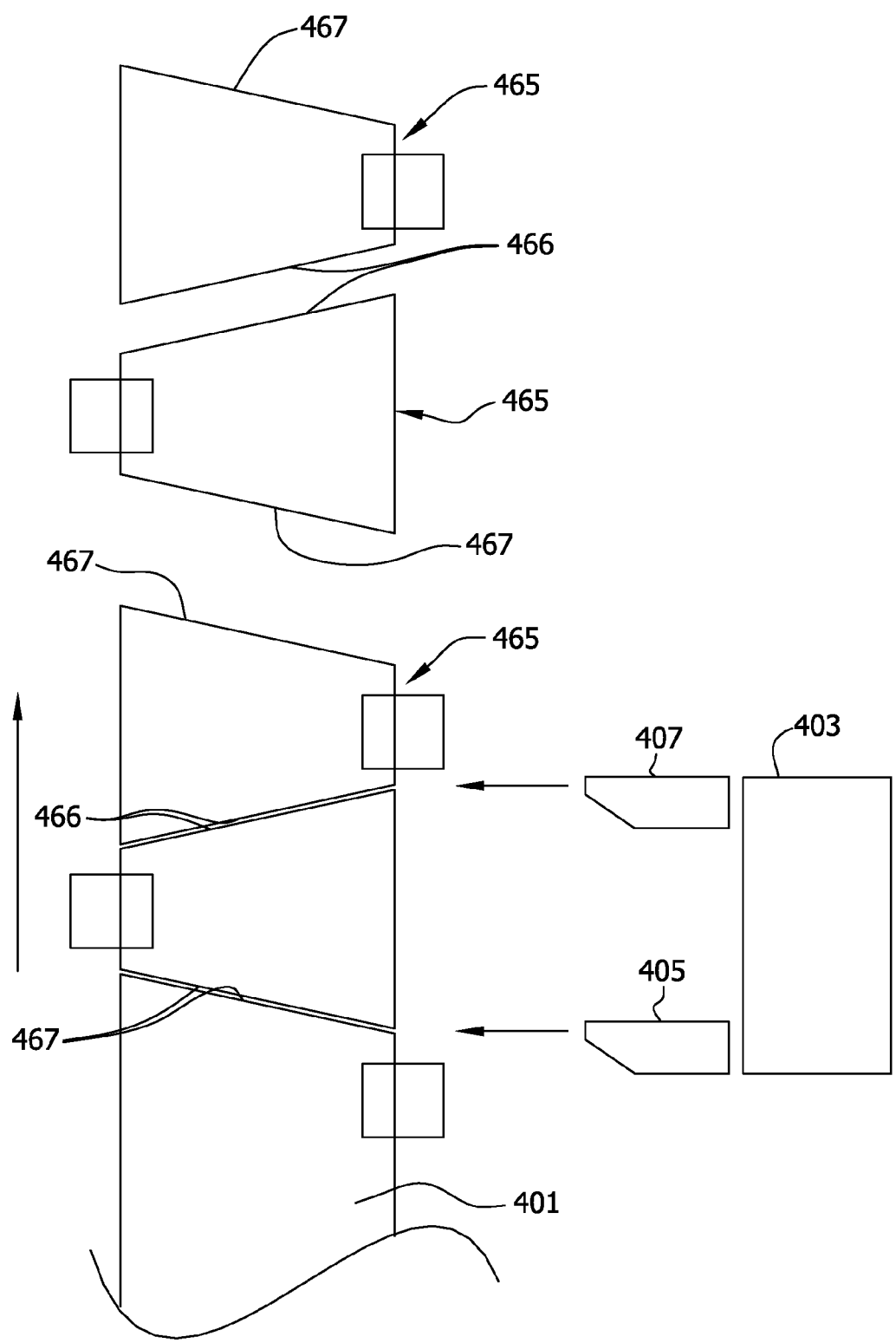
FIG. 8 is a schematic of a method of manufacturing another embodiment of hip panels from a web.

FIGS. 7-9 illustrate other embodiments of hip panels that can be manufactured from a web without waste. In particular, FIG. 7 is a schematic illustrating one suitable method of manufacturing the hip panels 165 of FIGS. 3 and 4 from a continuous web 301. The method is substantially similar to the method described above and illustrated in FIG. 6. That is, the web 301 is fed to a cutting apparatus 303 in a machine direction as illustrated by the direction arrow in FIG. 7. The web 301 is cut at a first location 305 with the cutting apparatus 303 to form a lower edge 167 of a trailing hip panel 165 and an upper edge 166 of a leading hip panel. The web 301 is subsequently cut at a second location 305 with the cutting apparatus 303 to form the lower edge 167 of the leading hip panel 165. The attachment portion 192 of the hip panel 165 is also formed by the cuts at the first and second locations 305, 307. As illustrated, the entire web 301 is used in manufacturing the hip panels 165 thereby eliminating waste.

FIG. 8 is a schematic illustrating a method of manufacturing yet another embodiment of a hip panel 465 from a continuous web 401 without producing waste. The web 401 of material suitable for use as hip panels is fed to a cutting apparatus 403 in a machine direction as illustrated by the direction arrow in FIG. 8. The web 401 is cut along a diagonal at a first location 405 by the cutting apparatus 403 to form an edge 467 of the hip panel 465. The web 401 is also cut along a diagonal at a second location 405 by the cutting apparatus 403 to form an opposite edge 466 of the hip panel 465. As seen in FIG. 8, the resulting hip panel 465 is generally frustum.

FIG. 9 is a schematic illustrating a method of manufacturing still another embodiment of a hip panel 565 from a continuous web 501 without producing waste. The web 501 of material suitable for use as hip panels is fed to a cutting apparatus 503 in a machine direction as illustrated by an arrow in the Figure. The web 501 is cut along a generally straight line at a first location 505 by the cutting apparatus 503 to form an edge 567 of the hip panel 565. The web 501 is also cut along a diagonal at a second location 505 by the cutting apparatus 503 to form an opposite edge 566 of the hip panel 565.

When introducing elements of the present invention or the preferred embodiment(s) thereof, the articles "a", "an", "the", and "said" are intended to mean that there are one or more of the elements. The terms "comprising," "including", and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A disposable absorbent article comprising:
an absorbent assembly having a bodyside liner, an outer cover, an absorbent structure disposed intermediate the liner and the outer cover, a first waist region, a second waist region, a crotch region disposed longitudinally between and interconnecting the first waist region and the second waist region, longitudinally opposite ends, and laterally opposite side edges;
a pair of hip panels for releaseably securing the first and second waist regions of the absorbent assembly together in a wear configuration of the article, one of the hip panels extending laterally outward from one of the side edges in one of the first and second waist regions of the absorbent assembly and the other hip panel extending laterally outward from the opposite side edge in said one of the first and second waist regions of the absorbent assembly, each of the hip panels comprising an upper edge, a lower edge, a fixed end attached to one of said first and second waist regions, and a free end, each of the upper and lower edges having a length and being curved upward along at least a portion of its length, the curved portions of the upper and lower edges being substantially identical with respect to each other; and a fastener component secured to each of the hip panels.

2. The disposable absorbent article as set forth in claim 1 wherein the curved portions of the upper and lower edges of the hip panels have a first radius of curvature adjacent the fixed end and a second radius of curvature adjacent the free end, the first radius of curvature being greater than the second radius of curvature.

3. The disposable absorbent article as set forth in claim 1 wherein each of the fastener components extends laterally outward beyond the free end of the respective hip panel.

4. The disposable absorbent article as set forth in claim 1 wherein the fixed end of each hip panel has a height in the range between about 25 mm and about 100 mm.

5. The disposable absorbent article as set forth in claim 4 wherein the height of the fixed end is about 65 mm.

6. The disposable absorbent article as set forth in claim 1 wherein each of the hip panels further comprises an attachment portion.

7. The disposable absorbent article as set forth in claim 6 wherein the attachment portion of each hip panel is generally rectangular.

8. The disposable absorbent article as set forth in claim 1 wherein the hip panels are constructed of a neck-bonded laminate material.

9. The disposable absorbent article as set forth in claim 1 wherein the hip panels are stretchable.

10. The disposable absorbent article as set forth in claim 1 wherein the first waist region is a front waist region, and the second waist region is a back waist region.

11. The disposable absorbent article as set forth in claim 1 wherein the upper edge of each of the hip panels is longitudinally offset from the longitudinal end in the back waist region of the absorbent assembly a distance in the range of about 0 mm to about 45 mm.

12. The disposable absorbent article as set forth in claim 11 wherein the distance between the longitudinal end in the back waist region of the absorbent assembly and each of the upper edges of the hip panels is about 35 mm.

13. A disposable absorbent article comprising:

an absorbent assembly having a bodyside liner, an outer cover, an absorbent structure disposed intermediate the liner and the outer cover, a first waist region, a second waist region, a crotch region disposed longitudinally between and interconnecting the first waist region and the second waist region, longitudinal opposite ends, and laterally opposite side edges; and a pair of hip panels for releaseably securing the first and second waist regions of the absorbent assembly together in a wear configuration of the article, one of the hip panels extending laterally outward from one of the side edges in one of the first and second waist regions of the absorbent assembly and the other hip panel extending laterally outward from the opposite side edge in said one of first and second waist regions of the absorbent assembly, each of the hip panels having a fixed end attached to the absorbent assembly at a location offset longitudinally from the longitudinal end in said one of first and second waist regions, and a free end disposed closer to a line including the longitudinal end in said one of the first and second waist regions than the fixed end in an opened and laid-flat configuration of the article.

14. The disposable absorbent article as set forth in claim 13 wherein the distance between the longitudinal end in said one of first and second waist regions of the absorbent assembly and the upper edges of each of the hip panels is in the range of about 0 mm to about 45 mm.

15. The disposable absorbent article as set forth in claim 14 wherein the distance between the longitudinal end in said one of first and second waist regions of the absorbent assembly and the upper edges of each of the hip panels is about 35 mm.

16. The disposable absorbent article as set forth in claim 13 wherein each of the hip panels curves as it extends away from the absorbent assembly.

17. The disposable absorbent article as set forth in claim 16 wherein each of the hip panels curves upward as it extends away from the absorbent assembly.

18. The disposable absorbent article as set forth in claim 13 wherein the article is a diaper.

19. The disposable absorbent article as set forth in claim 13 wherein each of the hip panels has a height at its free end and an overall height that is defined by its maximum projected height, the ratio of the overall height to the height at the free end being greater than 1.

20. The disposable absorbent article as set forth in claim 19 wherein the ratio of the overall height to the height at the free end is in the range of about 1.5 and 2.25.

21. The disposable absorbent article as set forth in claim 20 wherein the ratio of the overall height to the height at the free end is approximately 1.75.

\* \* \* \* \*